United States Patent [19]
Iandolo et al.

[11] Patent Number: 6,043,219
[45] Date of Patent: Mar. 28, 2000

[54] BROAD SPECTRUM CHEMOTHERAPEUTIC PEPTIDE

[75] Inventors: John J. Iandolo; Scott Crupper, both of Manhattan, Kans.

[73] Assignee: Kansas State University Research Foundation, Manhattan, Kans.

[21] Appl. No.: 08/931,999

[22] Filed: Sep. 17, 1997

Related U.S. Application Data

[63] Continuation-in-part of application No. 08/710,561, Sep. 19, 1996, abandoned.

[51] Int. Cl.$^7$ .......................... A61K 38/02; A61K 38/16; C07K 2/00; C07K 14/31
[52] U.S. Cl. ............................... 514/12; 514/2; 530/300; 530/324; 530/825
[58] Field of Search .................................. 530/300, 322, 530/324, 825; 514/2, 8, 12

[56] References Cited

U.S. PATENT DOCUMENTS

| | | | |
|---|---|---|---|
| 4,588,692 | 5/1986 | Cunliffe et al. | 514/2 |
| 5,231,013 | 7/1993 | Jung et al. | 435/71.3 |

OTHER PUBLICATIONS

R. Hickman, Isolation, Purification and Biological Properties ... Dissertation, Clemson University, pp. 61.63.79. Aug. 1983.
Cooper, Biotechnology and The Law, Deerfield: CBC. vol. 1, pp. 5B–41 through 5B–43, 1992.
Harris et al. Protein purification Methods. Oxford: IRL Press. pp. 9,10,57–63, 1989.
Sahl, Influence of the Staphylococclnlike Peptide Pep 5 . . . J. Bacter. vol. 162, No. 2, pp. 833–836, May 1985.
Bhunia, A. K., M. C. Johnson and B. Ray. J. Indust. Microbiol. 2:319–322 (1987).
Dajani, A.S., E. D. Gray and L. W. Wannamaker. J. Exp. Med. 131:1004–1015 (1970).
Sears, P.M., B. S. Smith, W. K. Stewart, R. N. Gonzalez, S. D. Rubino, S. A. Gusik, E. S. Kulisek, S. J. Projan and P. Blackburn. J. Dairy Sci. 75:3185–3190 (1992).
Lewus, C. B., A. Kaiser and T. J. Montville. Appl. Environ. Microbiol. 57:1683–1688 (1991).
Miles, H., W. Lesser and P. Sears. J. Dairy Sci. 75:596–605 (1992).
Hurst, A. Adv. Appl. Microbiol. 27:85–123 (1981).
Jung, G. Agnew. Chem. In the Ed. Engl. 30:1051–1068 (1991).
Tagg, J.R., A. S. Dajani and L. W. Wannamaker. Bacteriol. Rev. 40:722–756 (1976).
Rogolsky, M. B. B. Wiley. Infection and Immunity 15:726–32 (1977).
Jackson, M. P. and J. Iandolo. J. Bacteriol. 166:574–580 (1986).
Masterson, R., W.V. David, B.B. Wiley, M. Rogolsky, Infection and Immunity. 42:973–79 Aug. 26, 1997 (1983).

*Primary Examiner*—Jeffrey E. Russel
*Attorney, Agent, or Firm*—Hovey, Williams, Timmons & Collins

[57] ABSTRACT

Therapeutic proteinaceous substances produced by Staphylococcus (e.g., the active moiety of BacR1) having a molecular weight of from about 3 to 4 kilodaltons are disclosed. Also disclosed are methods of inhibiting the growth of procaryotic or eucaryotic cells using these substances.

15 Claims, 8 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 204 base pairs
      (B) TYPE: nucleic acid
      (C) STRANDEDNESS: double
      (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
      (A) ORGANISM: Staphylococcus aureus
      (B) STRAIN: UT0007

(vii) IMMEDIATE SOURCE:
      (B) CLONE: BacR1

(viii) POSITION IN GENOME:
      (A) CHROMOSOME/SEGMENT: pRW001
      (C) UNITS: bp (ix) FEATURE:
      (A) NAME/KEY: mat_peptide
      (B) LOCATION: 124..204

(xi) SEQUENCE DESCRIPTION: SEQ ID NO:1:

```
ATGAAAAATG AATTAGGTAA GTTTTTAGAA GAAAACGAAT TAGAGTTAGG TAAATTTTCA      60

GAATCAGACA TGCTAGAAAT TACTGATGAT GAAAGTATAT GCAGCTGGAA CACCTTTACC     120

TTATTGGGTG GAGCTGCCAC CGGGGTGATA GGTTATATTT CTAACCAAAC ATGTCCAACA     180

ACTGCTTGTA CACGCGCTTG CTAG                                           204
```

(2) INFORMATION FOR SEQ ID NO:2:

(i) SEQUENCE CHARACTERISTICS:
      (A) LENGTH: 81 base pairs
      (B) TYPE: nucleic acid
      (C) STRANDEDNESS: double
      (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
             (A) ORGANISM: Staphylococcus aureus
             (B) STRAIN: UT0007

(viii) POSITION IN GENOME:
             (C) UNITS: bp (xi) SEQUENCE DESCRIPTION: SEQ ID NO:2:

TTGGGTGGAG CTGCCACCGG GGTGATAGGT TATATTTCTA ACCAAACATG TCCAACAACT      60

GCTTGTACAC GCGCTTGCTA G                                               81

(2) INFORMATION FOR SEQ ID NO:3:

(i) SEQUENCE CHARACTERISTICS:
             (A) LENGTH: 26 amino acids
             (B) TYPE: amino acid
             (C) STRANDEDNESS: single
             (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
             (A) ORGANISM: Staphylococcus aureus
             (B) STRAIN: UT0007

(viii) POSITION IN GENOME:
             (C) UNITS: kb (ix) FEATURE:
             (A) NAME/KEY: Peptide
             (B) LOCATION: 1..26

(xi) SEQUENCE DESCRIPTION: SEQ ID NO:3:

Leu Gly Gly Ala Ala Thr Gly Val Ile Gly Tyr Ile Ser Asn Gln Thr
1               5                   10                  15

Cys Pro Thr Thr Ala Cys Thr Arg Ala Cys
            20                  25

(2) INFORMATION FOR SEQ ID NO:4:

(i) SEQUENCE CHARACTERISTICS:
             (A) LENGTH: 6755 base pairs
             (B) TYPE: nucleic acid
             (C) STRANDEDNESS: double
             (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
             (A) ORGANISM: Staphylococcus aureus
             (B) STRAIN: UT0007

(xi) SEQUENCE DESCRIPTION: SEQ ID NO:4:

-continued

```
AGAAAAAGAA AGGAAGAGAA GAAAACGAAA GAGAGGAAAC AGAACAGACA GCAGAAAACG      60

AGAGAAAGAA GCAGCGGAAC ACCACCAGGG GGAGCGCCAC CGGGGGAAGG AACAACCAAA     120

CAGCCAACAA CGCGACACGC GCGCAGGAAG GGAGAAGCAA AGGACACAAG AAAGAAGAAC     180

CAGAACAAAA AACAGAAAAG AACAAACCAA AAGAAGAAGA AACGAACCCA GAAAAGAAG      240

AAGGACAAGA GAAGGAAGAA GACCACAAAG CGAGAAAAGC GAAGGCGGA GACAACGGGA      300

ACAAGCAAAA AAAACAAAAC CAGCGAAAAA AAAGCGACGC GAAACGCAAG CCGCAGAAAG     360

AAGCGCAAAG AAAAAAAAAA AAGAAGACAA CACAGAAGAC AACACAAAAA GAAGAAAAA      420

ACAGGACACA AACGAAAGGG GGGGGACGAG AAAAAAAAAA GAGCAAAACG AAGAAAACCA     480

GAAAAAAACA AAACCGAAGA AAGAAAGAAA GAAACCAAAG CCAAGAAGAC CAAAAAGGGA    540

ACGCAAAACG GCGCCAGAAA AGAAAAAAAG CAAAAGCCAA CCACAGGAGA AGGAACAAAA    600

AAAAAAAGAA GCAGAGCAAA CACAAAGGAG AAGGGGGAGG CACCAACGAA AAAAAAAAGA    660

ACAAAAAAGA AAGAAGCCGG AAAGCGCAAG AAAAACGAAG CAAACAAAAC GGACAAAACG    720

GCCCACCAGA AAAACACACC CAAAAAAAGC GACAGAAAAA AAAAAAAGCA AAAAAGAAAA    780

CGAAGGAACA GGAACCCCAG CAACAAAAAA CAGACGGAAA AGGACGGAAA AAAACAAAAA    840

CACACCCCCA AAACAAAGAA GGCACCAAAA AAAAAGGCAA ACACCAAAAA AAAGGGCACG    900

CAAGAGAGAG AAAAAAGGGG AAAGGAAAAA AACCCAAGGA AGGGACCAAA AAGAAGGAAA    960

AAAAAAAAAA AACGGAGAAA CAGGAAAAAA AGGAAAACAA ACAGAGAAGG ACGAACAAAA   1020

CGAAACACGG ACCCGAACCA CAAAAAAAAG AAGCCAAGGC CCGAGGAAAA GAGACAAGAA   1080

AAAAAAGCAC AGAGGACACA GCGGAAGGAG AACCCACAAA GAACAAAAAG CAGAGAACAG   1140

AAAAAAAGCA CGGACCAAAC CCCAAAGAAG AAAGAAAAAA GAACGACAGA AGACAAAAGA   1200

CAAAGAGAAA AAAAAGCGGG CAAAAAGCAG ACCAAGAGAC GAACAAAAGA AAGGAAAAAG   1260

AGGACGAAAG AAAAAAAACA AGAGCACACC AAAGAACAGA CGAAAGAAAA GAAGACCGGA   1320

AACCAGCCAA AACGGAAGGA CCGCCCAAAG GAAGGGAGGA CCCAGGAGAG GCAGAAAAGG   1380

GCAGAACGGC CCCCAGCAAA CGGAAAACAA AAAAAACCAA AAGGAAAGAG GCAGAGGAAA   1440

AGACAAAAAG AGGAGAAAAC AACGACAAGA AAACAGCGGG AAGGAGCCGG AAGCAGGCAA   1500

AGGAGCCAAC GCGAAAGAC ACGAAAACAA AGGAAAAAAC AGCAAAAGCG AAAGAGAAGA     1560

AAAAAGAAAG AAGAGAAAGG CGACGAAGAC AGGGAGAGCG GAGCAAAAGA GAAAAAACCA   1620

AGAAGAACCG ACGAAAACAA AAAGAAAAGG AAAGAAGCAA AAAAAAAAAA GAAAAACACC   1680

CGGAAGCCAG GAAAAGCCAG AAGAGCAAAA AAAAACAAA AGCAGAAAAA GAAGAAAAAG     1740

AAGAACAAAA AACAAACAAA ACAAGGCAAA AAAGAAAAAG GCGGAAGACA AAAAAAACAC   1800

GCGGGCAAGG ACCGGACACA GCAAACGAAG GAAAAAGCGG AACAAAAGAG AAGAAGAAAA   1860

AAGCAAAGAA AAACCACGAG CCGAACCGCA GGAGAGGGAG ACGAAAAGAA GCAAAGACGA   1920

AAAAGAAACA CGAAAAGAAA AGAAAAAACA CGAGCCGCGA AGAAAACAA AGAGGAGAGG     1980

AGAAACACAG CCCAGGAAAA GACAGGAAAA CCGGAGAAAC AAGAAAGCAG AGGGAAAGAG   2040

CCCCCCAACG AGGGAAAGGC AAAGAAAAAA AAAAAAAGA GCCACCACAC AAAGCCAAAC     2100

AGAAGCGGAG GGGGAAAAGA ACGAAAAGAA GGCACCAGAA CAGAAAAAAA AGAACCAGGA   2160

AGAGAGGAGG GAAACAGAA AAGGGGGAAG AAACAAAGGA AGAAAAGGAA AGAAAAAAGC     2220

CGAAGGAACC GAAAGCCGGA AAGGCGCAAC GGAGAGCAAA GAAAAAACGA GAAGGACCAC   2280

AGAGGGAGAA AAAAAAAGAC AGAAAAGCAA GAAGAACGGA AGACCCAAAG AAACAAAAAC   2340

GAAACAACGG ACAAAAAAAA AACAAAGGCC AAACAAAGAA AGAAAGAAAA AGCACGAGGG   2400
```

-continued

```
AAGCAAACAA CAGCAACCCA AGCCACACAA AAAAAAGACA GCACAAACCA AAAACAAAAG    2460

AACAACCAAG AAAAGCAGGC GCAGAGAAAC GACAACAAAG AAAAAAAGGA AGAAGGGCAA    2520

ACGAAAGCCG CAAAAACCAG CGCCGCCCAG GAGAAAACGA AGAAAAGCAA ACCGCACAAG    2580

AAAAGGCCCA CAGGACGCAC AGAAGAGGCA CAAGGAGAAA CCACAAGCAA AAAAACGAAA    2640

CAGCAAGCAA AAACACAAAC CAAAGGACAG AGAGACAGAA GGAAGAGGCC AAAGACCAAC    2700

AGCAGACAAA AAGGAAGAAG GGGAACAGAA ACGACAAGAG AGGGCAACAG GACAAAAACG    2760

AAAGCAGGAA AAAAGAAGAA AACAAGAGGG GGGCAAAGAA CGGCCAAACG CCCACGCAAA    2820

CAAAAAACCA AGGGGAAAGA CAGGACAGGC GAGCAGACAG CGGCAGGCAC AAACAACAAA    2880

CACACGAAGC GACGGCAACG AAAAAGAAAC AGAAGAAGAA ACCCGAGGAG AACGAAAAGC    2940

AGACAAAGCA GCAGGAGAGA GAAAAAGAAG CACAGACACA CCAGAAAGCC CAGCAAAAAA    3000

CAAAAAGAAA AAGAGGGGAC ACAAGCAGGG GCAGCGGGAC AGGAAAACAC AAGGAAACAA    3060

GACCCGAACC CAGGGCAGCA AAGGGGGAG AGAAAACAAA AAAACAGAAA AAGACACAAG    3120

ACAACCACAA GAAGCAACCC AAAAGAACAA GGAAAGAAG GGGAACACA AGAAACGAAA    3180

AACAAACGGC CAACAGCCAA AACAAAAGCG CCAGGGAAAG ACAGAGCGAA AGGGGCAAGC    3240

AGGAGGCAAC GACAAAGAAA CAAAGCAAAA GCCGCAACCC AAAAAGAGGA GAAGCACCCA    3300

CGAAAGGCGC AGCACAGAAG ACGAACACGA GAAAAAGCAC CAAAACGAAG CCACGAGCAC    3360

GAAAGCAGAA AAAAGGAGGA CAGGAGAAAG GAAGGGCGCA CAAAGAAGAA AAAAAAGGAA    3420

AGAAAACAAA GCGAAAAAAA GGAGGGGAGG AGAAAAGAAA AAGAGAACAA AAAACACCGA    3480

GCAGAAGAAA AAAAAAAGGG AAAAAAAAAA CAAAAAAAAA AAACAGAAGA CAAGACGAGG    3540

AGAAAAAAAA AAAGAACAAG CAGACAACGA AGAAACAAGC GGAAAACACG AAAAAACGAG    3600

AACAGAGAGA AAAAAAAAAA ACCCAAGCAC AACCGCAAGC GACCAAAAAA AAAACGCCGA    3660

AACCAAACAG GAAAAAACCA AAAGAGAGAA AGAAAAAAAA AAAACGGAGC AAAAAGCGCA    3720

GAAAACGGA GGAAACAAGA AAAAAACCAA AAAAAGGGAA AAAGCAAAAA ACGCGGACAG    3780

ACCACAAAAA AAAAAGGGAC AGGAGAAAAG CAAAAGAAAA ACCAAACAAA AGAGAAGCAC    3840

GAAAAGAAAA AACAGGAAGA GCGAACAAAA AACCGGCACA AGAAGAAGAG GAGAAGGAGG    3900

CAACGAAACG AAAACCAAAA AGAGACCCAA AGCAACAAAG GCAGCGCAAC GCCAGGGCAC    3960

AGAGCAGAGA GAAAAACAAA ACGAAACCAA ACGAGGAAAC AGCCAGCCGA AAAAAAAAAA    4020

AACAAGAGAA CAGCGGAAAA AAACCAAGCA GACACAAACC CAAAAAAAGA ACAGCAGAAA    4080

GAGGGCAAAA ACCCCACCCC AAAAACAAA AAAGGCGCAA AAAAGGCACG AGCAGGAAAG    4140

CCAAAGAAAA GACCGGAACC AAAAACCAAA AACAACAGAA GGGAAGCAAG CAACCCACCC    4200

ACAACGACAG AAGGCAAAAG GAAAACGGGC GGAAAAACGA CCAAAAAAAA ACAAAAACAC    4260

ACAAGAGAGA AAAAAGGCCA CCGACAAAAC AGCCGAGCAA AAACCCCAGA AAACAAAAAG    4320

GAAAAAAAGC GAAAAAAAGA CACAAAGCCA ACAAAAGAAA GAAGAAAAAG CCGGAAAAAA    4380

GAAGAAAAAA AAGCAAAAAC AAGGAGAACC CCAACAAACA AGCAAAAAAA ACACAAGGAC    4440

GACAGGAAAA GCGAGAACCC AGAGAAAAAA GGGAAAAAAA CAAACAAAAA AAGGAAAGCA    4500

AAAACCAAAG CAGGAAGGCA AACAACACAA AAGAGGCGGA GACGGAAGAA AAAACACCCC    4560

GAAAAAAACA ACAAAAAGAC AACACAAAAC CAACCCAAAG AGAAGAAAGA AACACAACGA    4620

AAAAAGAAAA CGGGGAAGGA AGAGGAAACA GCCAGAGAAA CAGACAACCA CAGAACGGGA    4680

GGGGACCAGA ACAAAAAGAA GGCAAAACCA GAGAAGGGAC AAACCAGCAA ACAGGAACAA    4740
```

-continued

```
GAACACAAGA AAAAGAAAAA CAAGAAACCG AAACGGAAAA CACAAGACAG AACAAAAACG    4800

AAAAACGACA AAGAAAAAGC GGCCGACGGA CAAAAAAAGG AAGAGAGGAC CCCAGGAAGG    4860

AGACACCCCC CACACCCAGA AAAAAAAACA AGACAAGGAG ACGGAAAAAC ACAGAAAAAA    4920

GGAAAGCCAC GGCAAAGGAA GGCAAAACGA AAAAAGAAAA GAAAAGAACA GAAAAAAGGA    4980

GGAAGAAAAA AACCACAACG GGGGGGGGCA AGCAGGGACC AGGAGCAGGA CAGAAAAACG    5040

GGAAAAACAA AAAACAGCAA AAAGGCAAAA CCCAAAAGAA CCAAAAAACA GGGCAGGCCA    5100

AGCCGGCAAC ACACACAAGA CAACAAAGAG AGGGAACACA AAACCGGCAA AAGGGGAACA    5160

AAAAAGGAGG AAAGGGGGGA AAAAAGAGAA AAGGGACAGG GGGAGGGGCA GAAGGAAACG    5220

CCCAAAAAAA AGAAAAAACC GGAACCAGAA AAGCAGAAAC CAAGAAAAAG AAGGAGCGAA    5280

AAAGAAAACG GGCAAAAGCA GAAAAAGAAC AACACAACAA GGGGACAGAA CGGACAACAA    5340

AAACCGGAAA AGAAGCGGAA AACCAAAACG AACACCCGAA AAGACGAAGG ACAAGCAAAG    5400

CAACGAAAAG AGACAAGGCG AAAAGAAAAA AAGAAAAAAA AAAAGAAACA AAACGCCGGG    5460

AAGGCCAGGA AGAAAGGGCA AGCGAAGAAG GGAGAAACAG AACCAAGCGA CAGAGAGAAA    5520

AGGAACGGGA ACCCACAAGC AGGGAGGGAA AACAAAAAAA AAAAAAACGC CAAAAAAAAC    5580

AAAGAAGCGG GAGGGGCACA AACAGACAGC AAGAAGAAAA AAAAAAACAG GGGAACACAG    5640

GAGGCGCGAA CGACACAAAA AAAACAGCAC AAAAACCCAA GAACACGACA AAAGGAGAAA    5700

AAGAAAAAAG ACAACCAAGA CAAGAAAAAA GAAAACAAAG ACAAACAAGA AAAGAAAAGA    5760

AGAAAAAAAA CCAGCGACCC CGACAGAAAA GAAGAGCAGA GGGAAACGGA CAACAACAGG    5820

GACAGGGACA ACACCCAGAA ACACCAACAA CACGAACCAA AGAGAAAGCA AGAGAGCAAA    5880

AAAACACAAC AGGGAAGAGG AAAACCAAAG AGGAAGAGCA AAAAAGAAAA AGGCACAGCC    5940

AGAGAAACCA AGAAAGGGAA AAAAACACGA ACGGAAAAAA ACAAGAGGAA AAGAAGAACA    6000

AAAAAGGAGA ACGAGAAAAA CAAAGAAACA GGAACGAGCA AGAAGAAGAA CAACAAAAAA    6060

AAAGAAGGAG GGAAGGAAGA AAGGAGCAGG AAAAGACCAA GAAAAAACAC CAACCGAAAA    6120

AGCACGGAGA GAAGGAACGA AGAAGGAAAA GAAGAACCCA AAAAAAAACA AAACGGGACA    6180

GAGCACAAAG ACCAAAAACA ACAACGAAAA ACGACAAGAA ACAAAACACA AAGAGAGAAA    6240

AAGAAAAGAA AAAAAACGCA GGAGAAACAA AAGCAGGGAA ACAAGCAAAA AAACCCGCAA    6300

AGACGAGCCC ACAAAAGAGG AAGAAACCGC GAAAAAAAGA AAAAAAAAAA GCCAAAAACA    6360

AAAAGGAACA ACAAGCAAAA AGAAGAAGAA AAGGGAAGAA AAAAGAGGAA AACAGAGAGA    6420

ACAAAAGCCA AAAAAACAAC GAAGCGGAGA AGAAAGAGCA AAAACAAACA CGCAAAAGGG    6480

CAAAAAAGCA CGACCAAACA AAAGACAAAC AAGCACAACA AAGCGAACAA CACAACCCAA    6540

AAAAAAGAGA ACAGAAAAAC AAACACGAGA ACAACAAAGA AAGGGAGGCA AAAGAACAAA    6600

ACAAAAAACA CGAAGAACAC GGGGAAAAAA AGAGGACACA AAGGAAAACA ACACCCCCCC    6660

CCCCAAGCGA CCCAAAAAAA GAGCCAACAA AACAGACAAA CAGAGGGCAG CGCCGCAGCA    6720

CACCACCAGA AAGAGACACA CAAAGGACCA AAAAA                              6755
```

BROAD SPECTRUM CHEMOTHERAPEUTIC PEPTIDE

RELATED APPLICATION

This application is a continuation-in-part of application Ser. No. 08/710,561 filed Sep. 19, 1996, now abandoned.

This invention was made with government support under Grant Al-17474 awarded by the Department of Health and Human Services/National Institutes of Health. The government has certain rights in the invention.

BACKGROUND OF THE INVENTION

1. Field of the Invention

The present invention is broadly concerned with therapeutic proteinaceous substances produced by Staphylococcus, and with methods of inhibiting the growth of eucaryotic or procaryotic cells using these substances. More particularly, the invention in its preferred form is directed to BacR1, a 3.4-kilodalton therapeutic proteinaceous substance produced by Staphylococcus aureus UT0007. The sequence of the BacR1 gene is set forth in SEQ ID No. 2, while the sequence of the BacR1 peptide is set forth in SEQ ID No. 3.

2. Description of the Related Art

Bacteriocins and colicins are antimicrobial agents produced by gram-positive bacteria and gram-negative bacteria, respectively. Each of these agents inhibits or kills species which are closely related to the organism producing it (Jack et al. 1995. Microbiol. Rev. 59:171–200). Colicins generally have (1) a narrow range of antimicrobial activity, (2) bacteriocidal activity, (3) a protein component expressing the antimicrobial activity, (4) the ability to attach to specific cell-surface receptors, (5) plasmid-borne genetic determinants, and (6) immunity mechanisms to avoid cell suicide (Tagg et al. 1976. Bacteriol. Rev. 40:722–756).

Bacteriocins and bacteriocin-like inhibitory substances are similar in nature to colicins. However, they do not possess all of the colicin characteristics noted above (Jack et al. 1995. Microbiol. Rev. 59:171–200). They generally exhibit a broad range of antimicrobial activity against gram-positive bacteria, and in some cases also inhibit gram-negative species. Genes encoding bacteriocin usually are arranged in operons located on plasmids. For example, the operons encoding the bacteriocins nisin (Engelke et al. 1992. Appl. Environ. Microbiol. 58:3730–3743) and epidermin (Augustin et al. 1992. Eur. J. Biochem. 204:1149–1154), in addition to containing the respective bacteriocin structural genes, contain genes responsible for post-translational modifications, processing, cellular export, and host cell immunity. Most bacteriocins are small cationic peptides that are relatively heat stable, sensitive to proteolytic enzymes, non-antigenic, and very hydrophobic (Jack et al. 1995. Microbiol. Rev. 59:171–200; Tagg et al. 1976. Bacteriol. Rev. 40:722–756). High molecular weight bacteriocins consisting of proteins complexed with lipids and/or carbohydrates also have been identified (Jack et al. 1995. Microbiol. Rev. 59:171–200).

The majority of research regarding bacteriocins has focused on those produced by the lactic acid bacteria, since these bacteriocins have potential as food preservatives (Hurst et al. 1981. Adv. Appl. Microbiol. 27:85–123). Additionally, several staphylococcal bacteriocins have been identified, including the staphylococcins 412 (Gagliano et al. 1970. J. Bacteriol. 104:117–125), 462 (Hale et al. 1973. Antimicrob. Agents Chemother. 4:634–640), C55 (Dajani et al. 1970. Infect. Immun. 1:485–490), and BacR1 (Rogolsky et al. 1977. Infect. Immun. 15:726–732). Although the bacteriocin BacR1 has been identified, it has not been isolated or well characterized. Furthermore, no pragmatic uses for BacR1 have been proposed in the prior art. For example, the Rogolsky et al. paper reported a maximum specific activity for the crude preparation of only 46 AU/mg; moreover, the sequence of the BacR1 gene and the corresponding peptide have not been identified.

SUMMARY OF THE INVENTION

The present invention contemplates using staphylococcal bacteriocins such as BacR1 as therapeutic agents. The invention concerns at least partially purified therapeutic proteinaceous substances produced by Staphylococcus (e.g., S. aureus), each having a molecular weight under 4 kilodaltons. In preferred embodiments, each substance is dispersed in a liquid wherein the liquid has a specific activity of at least about 1000 antimicrobial units per milligram of protein (more preferably at least about 10,000 antimicrobial units per milligram of protein, still more preferably at least about 30,000 antimicrobial units per milligram of protein, and most preferably from about 30,000–45,000 units per milligrams), is purified from cell cultures, is essentially protein, and has a molecular weight of about 3.4 kilodaltons. Preferably, amino acid residues selected from the group consisting of alanine, threonine, glycine and cysteine make up at least about 40% of the amino acid residues of the substances of the invention.

Each substance at a concentration of 640 antimicrobial units (AU)/ml in an aqueous solution retains essentially all of its antimicrobial activity after one or more of the following treatments: (1) heat treatment at 95° C. for 15 minutes, (2) treatment at pHs ranging from 3 to 11 at room temperature for 1 hour, (3) treatment with 6M urea at room temperature for 1 hour, and (4) treatment with deoxyribonuclease, ribonuclease, or lysostaphin at a concentration of 1 mg/ml at room temperature for 1 hour. Additionally, each substance at a concentration of 640 AU/ml in an aqueous solution loses essentially all of its antimicrobial activity after being treated at room temperature for 1 hour with proteinase K or trypsin at a concentration of 1 mg/ml.

Each substance at a concentration of 1280 AU/ml has antimicrobial activity against one or more of the following organisms: Bacillus subtilis Marburg, Bordetella brochoseptica, Bordetella pertussis, Corynebacterium diphtheriae, Corynebacterium pseudotuberculosis Whetten 1, Corynebacterium renale, Haemophilus parasuis, Moraxella bovis, Pasteurella multocida, Staphylococcus aureus 502A, Staphylococcus aureus 8325, Staphylococcus aureus RN4220, Staphylococcus intermedias, Streptococcus porcinus, and Streptococcus suis. This antimicrobial activity inhibits microbial growth, preferably by preventing the growth of the microorganism or by killing the microorganism.

In the most preferred embodiment, the substance is an active moiety of BacR1. BacR1 is a 26-mer proteinaceous substance produced by S. aureus UT0007 having a molecular weight of approximately 3.4 kilodaltons. S. aureus UT0007 has been deposited in the American Type Culture Collection, Rockville, Md. under the terms of the Budapest Treaty and has been accorded Accession No. 55800.

The sequence of BacR1 gene has been determined by N-terminal sequencing of the purified BacR1 protein, with back-translation and plasmid analysis. The BacR1 gene with its leader sequence is set forth in SEQ ID No. 1. SEQ ID No. 2 sets forth the BacR1 gene itself, without the leader sequence. The deduced sequence of the BacR1 peptide is given in SEQ ID No. 3. Accordingly, the invention includes isolated and/or substantially purified oligonucleotides (DNA molecules) which encode for BacR1 peptide (e.g., SEQ ID No. 2 and equivalents thereof based upon the degeneracy of the translation code), as well as essentially pure (typically at least 95% pure) recombinantly-derived peptides having the BacR1 sequence (SEQ ID No. 3) and those having at least about 80% sequence identity with SEQ ID No. 3. Such recombinantly-derived peptides may be produced by construction of an appropriate expression vector (e.g., a plasmid) containing an oligonucleotide or operon coding for BacR1, and transformation of such vector into host cells for BacR1 expression.

The invention also includes methods of inhibiting the growth of procaryotic or eucaryotic cells in an environment capable of sustaining such growth. These methods comprise administering to this environment a cellular growth-inhibiting amount of at least one of the substances (e.g., applying at least one of the substances topically on skin to control bacterial growth, using at least one of the substances as an antibiotic to prevent or eradicate bacterial infection in an animal, and using at least one of the substances, either chemically modified or unmodified, as an anti-cancer agent). Cellular growth is preferably inhibited by either preventing the growth of the cells or by killing the cells.

DETAILED DESCRIPTION OF THE PREFERRED EMBODIMENTS

The following examples describe the purification and characterization of BacR1, a therapeutic proteinaceous substance produced by *S. aureus* UT0007, and its use in inhibiting the growth of cells. The examples are set forth by way of illustration only, and nothing therein shall be taken as a limitation upon the overall scope of the invention.

EXAMPLE 1

Bacterial Strains and Media:

*S. aureus* UT0007 harbors pRW001 which encodes the genetic determinants for BacR1 production. This strain is maintained on Typticase Soy Agar (TSA). For BacR1 production, the strain is propagated at 37° C. with shaking at 220 rpm in 2X-YT medium [16 g/L Bacto-tryptone (Difco Laboratories, Detroit, Mich.), 10 g/L Bacto-yeast extract (Difco Laboratories, Detroit, Mich.), and 5 g/L NaCl]. *Corynebacterium renale* ATCC 19412 was used as the indicator strain in bactericidal assays (see below) and is routinely grown at 37° C. in brain heart infusion media (Difco Laboratories, Detroit, Mich.) containing 0.3% Tween-80 (BHT-80).

EXAMPLE 2
Bactericidal Assay of BacR1 (Plate Method):

Bactericidal activity of BacR1 was determined by plate dilution analysis on BHT-80 agar plates containing *C. renale* as previously described [Mayr-Harting et al. 1972. In J. R. Norris and D. W. Ribbons (ed.), Methods in Microbiology, vol. 7A, p. 315–422. Academic Press, Inc., New York; Tagg et al. 1971. Appl. Microbiol. 21:943]. To prepare *C. renale* plates, 100 µl of an overnight culture of *C. renale* were added to 20 ml of liquified BHT-80 agar held at 45° C. The inoculated agar was poured into Petri dishes. After solidification, wells having a diameter of 3 mm were bored in the agar with a gel punch. Bactericidal activity was assayed by pipetting 25 µl of serially diluted preparations of BacR1 into each well and incubating the plates at 37° C. overnight. Bactericidal activity was evident the next day as a zone of growth inhibition surrounding the well. This activity was measured in AU, defined as the reciprocal of the highest dilution demonstrating inhibitory activity.

Figure 1:
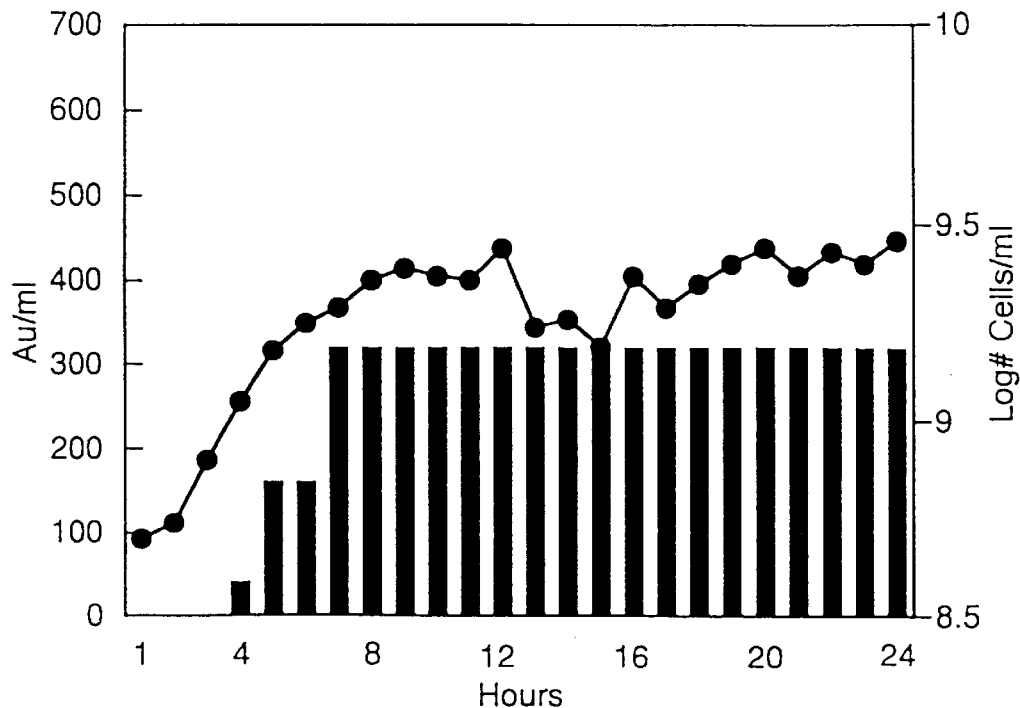
FIG. 1 includes a pair of graphs illustrating the growth of *S. aureus* UT0007 and corresponding secretion of BacR1; an overnight culture of *S. aureus* UT0007 was used to inoculate 2X-YT media to an initial $A_{550}$ of 0.05 and the culture was incubated at 37° C. with shaking; at respective times, the log number of cells (-●-) was determined and BacR1 activity (bars) was measured by bactericidal assay (plate method)

EXAMPLE 3
Production of BacR1:

The propagation of *S. aureus* UT0007 in 2X-YT media resulted in maximal levels of BacR1 being detected after 7 h of growth (FIG. 1). Although de novo synthesis of BacR1 was not directly examined, it appears that production of BacR1 is tightly regulated because production ceases after approximately 7 h. Prolonged incubation of filter-sterilized media from exponential phase cultures and from several stages of stationary phase cultures did not result in the loss of BacR1 activity. Therefore, BacR1 activity does not increase or decrease after about 7 h in culture. The stability of BacR1 is further demonstrated by the continual observation of maximal bactericidal activity up to 24 h in culture. This stability allowed the culture to be harvested at convenience without measurable losses in BacR1 activity.

Figure 2:
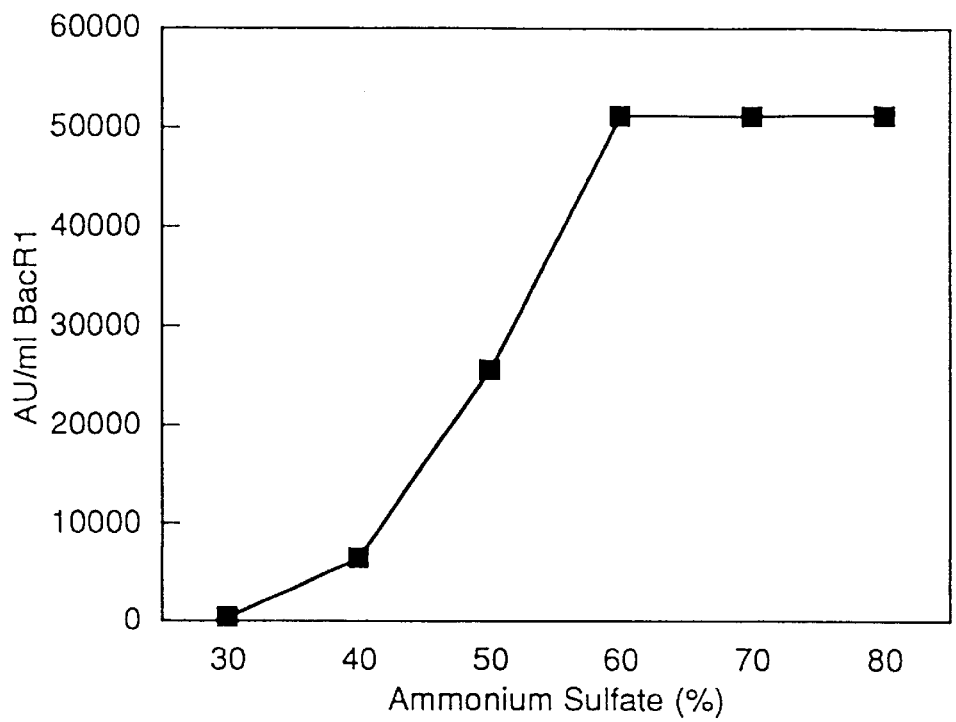
FIG. 2 includes a graph illustrating the ammonium sulfate precipitation of BacR1 activity; supernatant from an 18 h overnight culture of *S. aureus* UT0007 was divided into 50 ml volumes, and respective amounts of solid ammonium sulfate were added at room temperature with constant stirring to each aliquot to reach respective levels of saturation; once equilibrium was obtained, precipitated protein was collected by centrifugation at 9,000× g for 20 min at 4° C.; precipitates were resuspended in 0.5 ml of distilled water and BacR1 activity (-■-) of each fraction was measured by bactericidal assay (plate method)

EXAMPLE 4
Purification of BacR1:

An overnight culture of *S. aureus* UT0007 was used to inoculate one liter of 2X-YT medium to an $A_{550}$ of 0.05. The culture was incubated at 37° C. for 12–18 h with shaking at 220 rpm, and the cells were removed by centrifugation at 5,000× g for 10 min. The clarified culture supernatant was filter sterilized by passage through a 0.45 µm filter. Solid ammonium sulfate was added to the filter-sterilized supernatant to 60% saturation at room temperature to precipitate the BacR1 activity. The mixture was stirred for approximately 20 min until all of the ammonium sulfate was dissolved. This precipitation step provided a convenient way to concentrate large sample volumes without significant loss of total BacR1 activity. The use of ammonium sulfate concentrations greater than 60% did not result in any measurable increase in BacR1 activity relative to the activity obtained using 60% ammonium sulfate (FIG. 2).

After ammonium sulfate precipitation, a floating pellicle composed of protein and lipid was removed from the surface of the mixture. The mixture was then centrifuged at 9,000× g for 20 min at 4° C. The supernatant was discarded and the precipitate was dissolved in a minimal volume of 25% acetonitrile-10 mM sodium phosphate, pH 3.0. After centrifugation at 9,000× g for 10 min at 4° C. to remove insoluble protein, the sample was subjected to ion-exchange chromatograpy using a CM300 cation-exchange column (250 mm×10 mm) (SynChrom, Inc., Lafayette, Ind.).

After passing the sample through the CM300 column, the column was subjected to an increasing gradient of NaCl in acetonitrile using two buffers, buffers A and B. Buffer A consisted of 25% acetonitrile-10 mM sodium phosphate, pH 3.0, and buffer B consisted of buffer A containing 1 M NaCl. The elution conditions consisted of 0 M NaCl for the first 20 min and 1 M NaCl over the next 35 min (100% buffer A/0% buffer B for 0 to 20 min, and 0% buffer A/100% buffer B for 20 to 55 min). Fractions were collected and taken to dryness by evaporation, resuspended in 0.5 ml distilled water, and analyzed for BacR1 activity.

Figure 3:
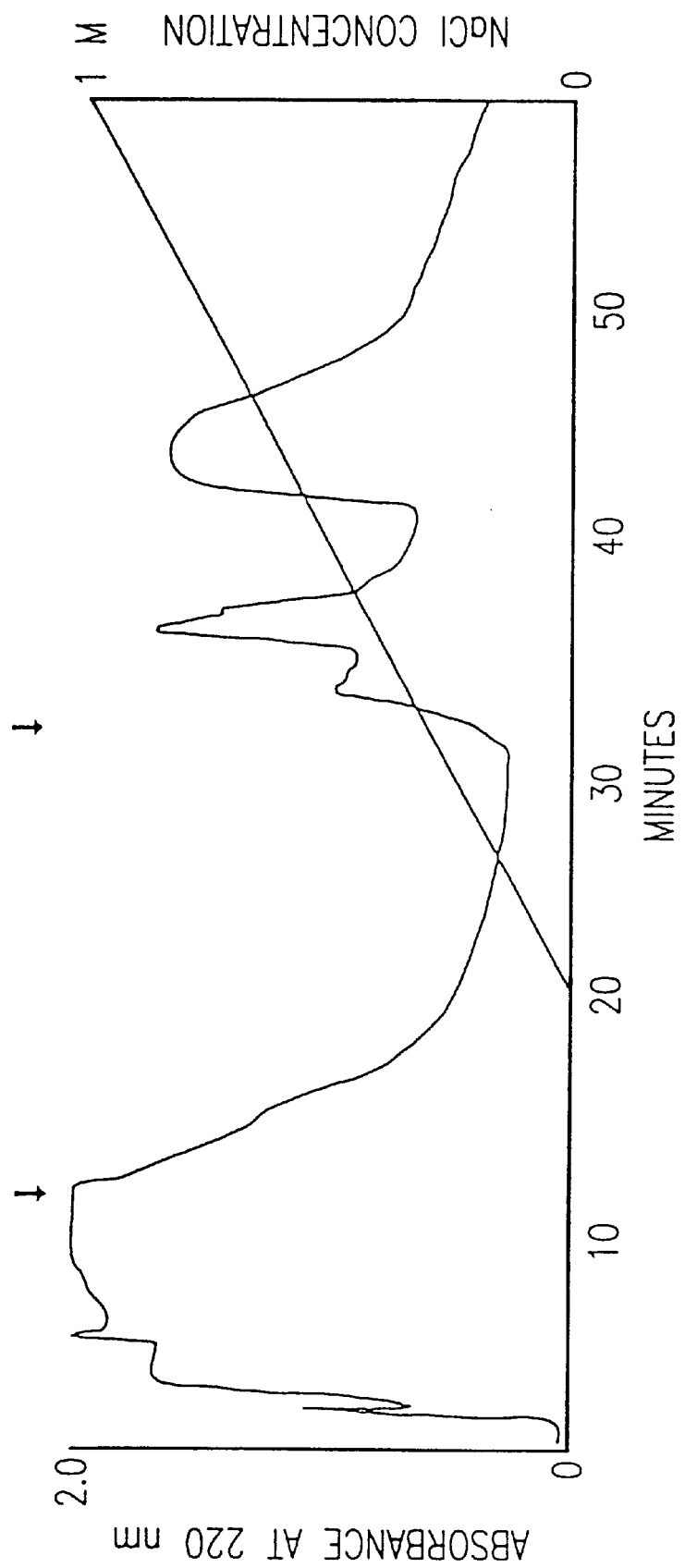
FIG. 3 includes a pair of graphs illustrating the elution profile of ammonium sulfate-concentrated BacR1 activity after CM300 cation-exchange chromatography using a NaCl gradient; the $A_{220}$ and the BacR1 activity of 2-ml fractions were determined; BacR1 was measured by bactericidal assay (plate method); the arrows indicate the beginning and end of active fractions.

As shown in FIG. 3, BacR1 activity did not bind to the cation-exchange column and eluted over several fractions. Also, BacR1 activity did not bind to an anion-exchange column (data not shown). Although binding could not be achieved with either ion-exchange column, cation-exchange chromatography at pH 3 removed a significant amount of contaminating protein and resulted in the best overall purification step (Table 1).

Figure 4:
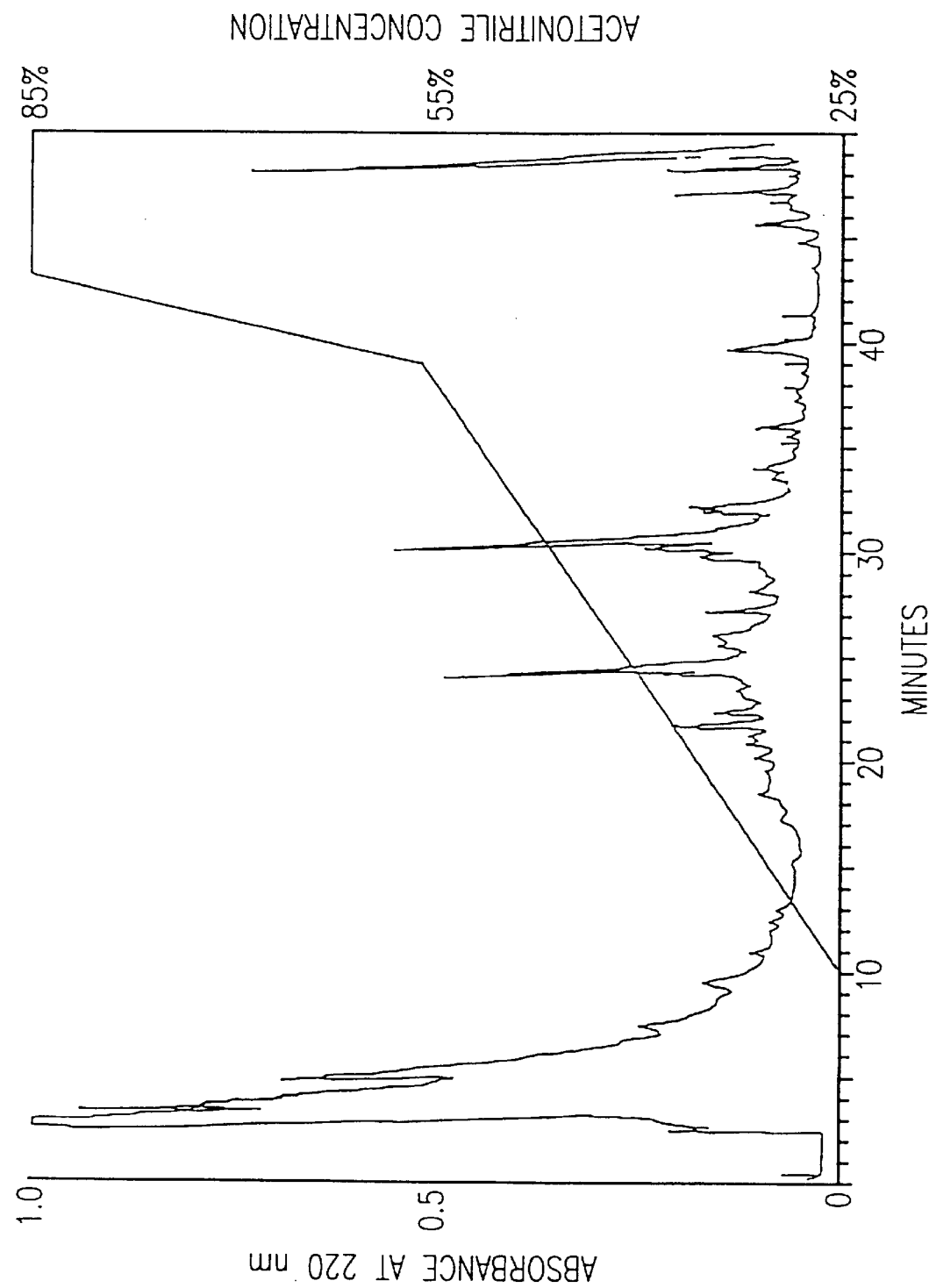
FIG. 4 includes a pair of graphs illustrating the elution profile of CM300-purified BacR1 activity after C4 reverse phase chromatography using a 1% per minute acetonitrile gradient; the $A_{220}$ and the BacR1 activity of 1-ml fractions were determined; BacR1 activity was measured by bactericidal assay (plate method); BacR1 activity eluted in fractions 25 and 26.

Fractions containing peak BacR1 activity were pooled, concentrated by evaporation, and passed through a C4 reverse-phase chromatography column (250 mm×4.6 mm; Vydac, Hesperia, Calif.). The column was then subjected to an increasing acetonitrile gradient using two buffers, buffers A1 and B1. Buffer A1 consisted of 25% acetonitrile-0.1% trifluoroacetic acid and buffer B1 consisted of 85% acetonitrile-0.1% trifluoroacetic acid. The gradient was increased from 25% to 85% acetonitrile at a rate of change of 1%/min. The elution conditions consisted of 25% acetonitrile for the first 10 min, 55% acetonitrile for the next 30 min, and 85% acetonitrile over the final 5 min (100% buffer A1/0% buffer B1 for 0 to 10 min, 50% buffer A1/50% buffer B1 for 10 to 40 min, and 0% buffer A1/100% buffer B1 for 40 to 45 min). As shown in FIG. 4, BacR1 activity eluted in fractions 25 and 26. C4 reverse-phase chromatography resulted in a significant increase in BacR1 specific activity (Table 1).

Figure 5:
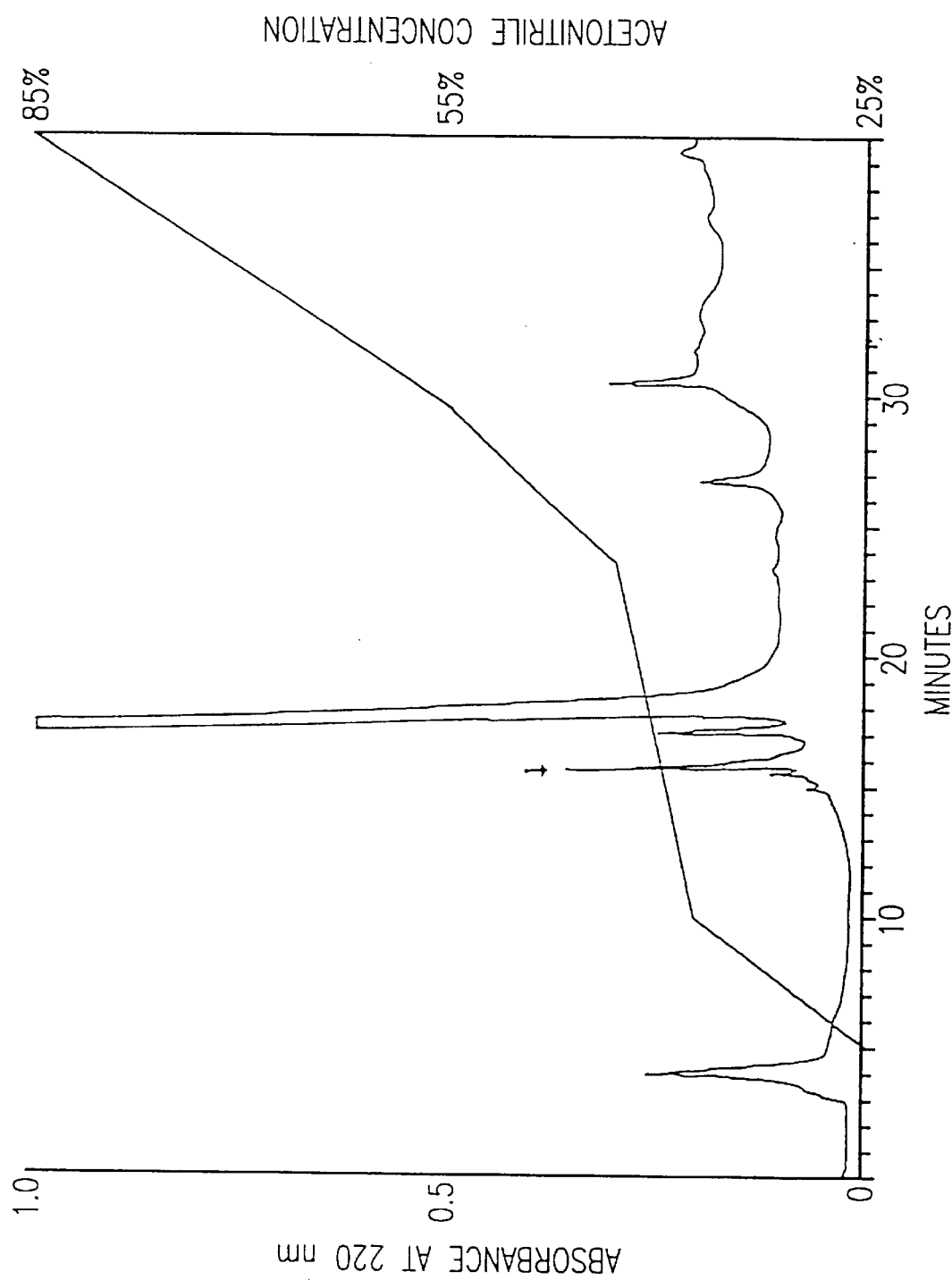
FIG. 5 includes a pair of graphs illustrating the elution profile of C4-purified BacR1 activity (pooled fractions 25 and 26 described above) after a second cycle of C4 reverse phase chromatography using a 0.5% per minute acetonitrile gradient; the $A_{220}$ and the BacR1 activity of 1-ml fractions were determined; BacR1 activity was measured by bactericidal assay (plate method); the arrow indicates the BacR1 peak.

Fractions 25 and 26 were pooled and concentrated by evaporation. Final purification was then achieved by subjecting fractions 25 and 26 to a second cycle of C4 reverse-phase chromatography using an acetonitrile gradient that increased from 25% to 55% acetonitrile at a rate change of 0.5%/min. The elution conditions consisted of 25% acetonitrile for the first 5 min, 37% acetonitrile for the next 5 min, 43% acetonitrile for the next 14 min, 55% acetonitrile for the next 6 min, and finally 85% acetonitrile for the final 10 min (100% buffer A1/0% buffer B1 for 0 to 5 min, 80% buffer A1/20% buffer B1 for 5 to 10 min, 70% buffer A1/30% buffer B1 for 10 to 24 min, 50% buffer A1/50% buffer B1 for 24 to 30 min, and 0% buffer A1/100% buffer B1 for 30 to 40 min). A single fraction contained the BacR1 activity (FIG. 5). When this fraction was re-applied to the C4 column using the same elution conditions, a single homogeneous peak was detected (data not shown).

The peak fraction of BacR1 activity was taken to dryness by evaporation. The resultant pellet was resuspended in distilled water, and total BacR1 activity and total protein concentration were determined. Protein concentrations were determined either by measuring the $A_{280}$ of the solution or by using a DC protein assay kit (Bio-Rad, Richmond, Calif.). The final purification step resulted in a BacR1 specific activity of 37,450 (AU/mg) with a total yield of 0.0047% (Table 1). The molecular weight of purified BacR1 was estimated to be 3362 daltons by mass spectrometry (data not shown). Mass spectrometry was carried out using a Lasermat matrix-assisted laser-desorption mass spectrometer at the Kansas State University Biotechnology facility.

BacR1 purified through the final purification step as described above is referred to hereinafter as "finally purified" BacR1.

TABLE 1

Purification of BacR1.

| Purification Stage | Total Protein (mg/ml) | Total Activity (AU)[a] | Specific Activity (AU/mg)[b] | Yield % | Fold Purification |
|---|---|---|---|---|---|
| Supernatant (1 L) | 2100 | 320,000 | 152 | 100 | 1 |
| Ammonium Sulfate | 211.4 | 266,240 | 1259 | 83.2 | 8.3 |
| Cation Exchange | 4.11 | 28,620 | 6963 | 9.3 | 45.8 |
| C4 Reverse-Phase (1st cycle) | 0.24 | 3994 | 16,642 | 0.0125 | 109.5 |
| C4 Reverse-Phase (2nd cycle) | 0.04 | 1498 | 37,450 | 0.0047 | 246.4 |

[a]Determined by bactericidal assay (plate method).
[b]Specific activity is AU divided by the total protein.

EXAMPLE 5

SDS-PAGE Bioassay of BacR1:

Purified preparations of BacR1 were subjected to electrophoretic analysis by SDS-PAGE. After electrophoresis, gels were either silver stained (Blum et al. 1987. Electrophoresis 8:93–99) or bioassayed using a slight modification of the method of Bhunia et al. (1987. J. Indust. Microbiol. 2:319–322). Briefly, each protein sample was electrophoresed in a 10–20% SDS-PAGE gradient gel (Bio-Rad, Richmond, Calif.) as previously described (Laemmli et al. 1970. Nature. 227:680–685). After electrophoresis, SDS was removed by soaking the gel in 20% isopropanol-10% acetic acid in water for 2 h, followed by rinsing in distilled water for 4 h. The gel was then placed on a BHT-80 agar plate and overlaid with BHT-80 top agar (0.7% agar) containing *C. renale*. After incubation at 37° C. overnight, the plate/gel combination was examined for zones of growth inhibition.

Figures 6A, 6B:
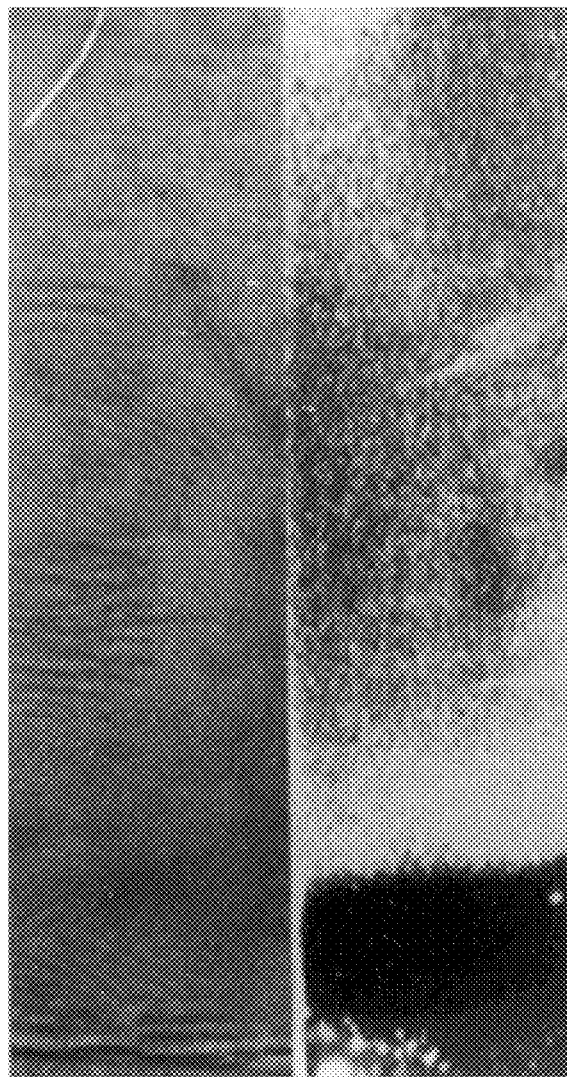
FIGS. 6 (A and B) include a photograph of a silver-stained SDS-PAGE gel of finally purified BacR1 (FIG. 6A) and a photograph of an SDS-PAGE gel of finally purified BacR1 overlaid with BHTA top agar seeded with *C. renale* (FIG. 6B)

Finally purified BacR1, when analyzed by SDS-PAGE, was not stainable with either coomassie blue or silver (FIG. 6, panel A) but possessed BacR1 activity (FIG. 6, panel B). The estimated molecular weight of purified BacR1 (3362 daltons) correlated well with the position of bactericidal activity shown on the SDS-PAGE gel in FIG. 6, panel B.

EXAMPLE 6

Preparative isoelectric focusing:

Isoelectric focusing of ammonium sulfate-precipitated culture supernatants of *S. aureus* UT0007 was carried out on a Rotofor isoelectric focusing cell (Bio-Rad, Richmond, Calif.) in order to define certain biophysical characteristics of BacR1. Concentrated culture supernatants were dialyzed overnight in 3,500 molecular-weight-cutoff dialysis tubing (SpectraPor, Los Angeles, Calif.) against 4 L distilled water at 4° C. The dialyzed sample was centrifuged at 9,000× g for 10 min at 4° C. to remove insoluble material, and the supernatant was diluted to a total volume of 55 ml with distilled water. Ampholytes (pH 3–10) (Fisher, St. Louis, Mo.) were added to a final concentration of 1% and the sample was loaded into the Rotofor cell for focusing at 12 W constant power at 4° C. The initial conditions were approximately 600 V and 35 mA; upon equilibrium the values were approximately 1200 V and 15 mA. Twenty individual fractions were harvested and the total protein, pH, and BacR1 activity for each fraction was determined.

Figure 7:
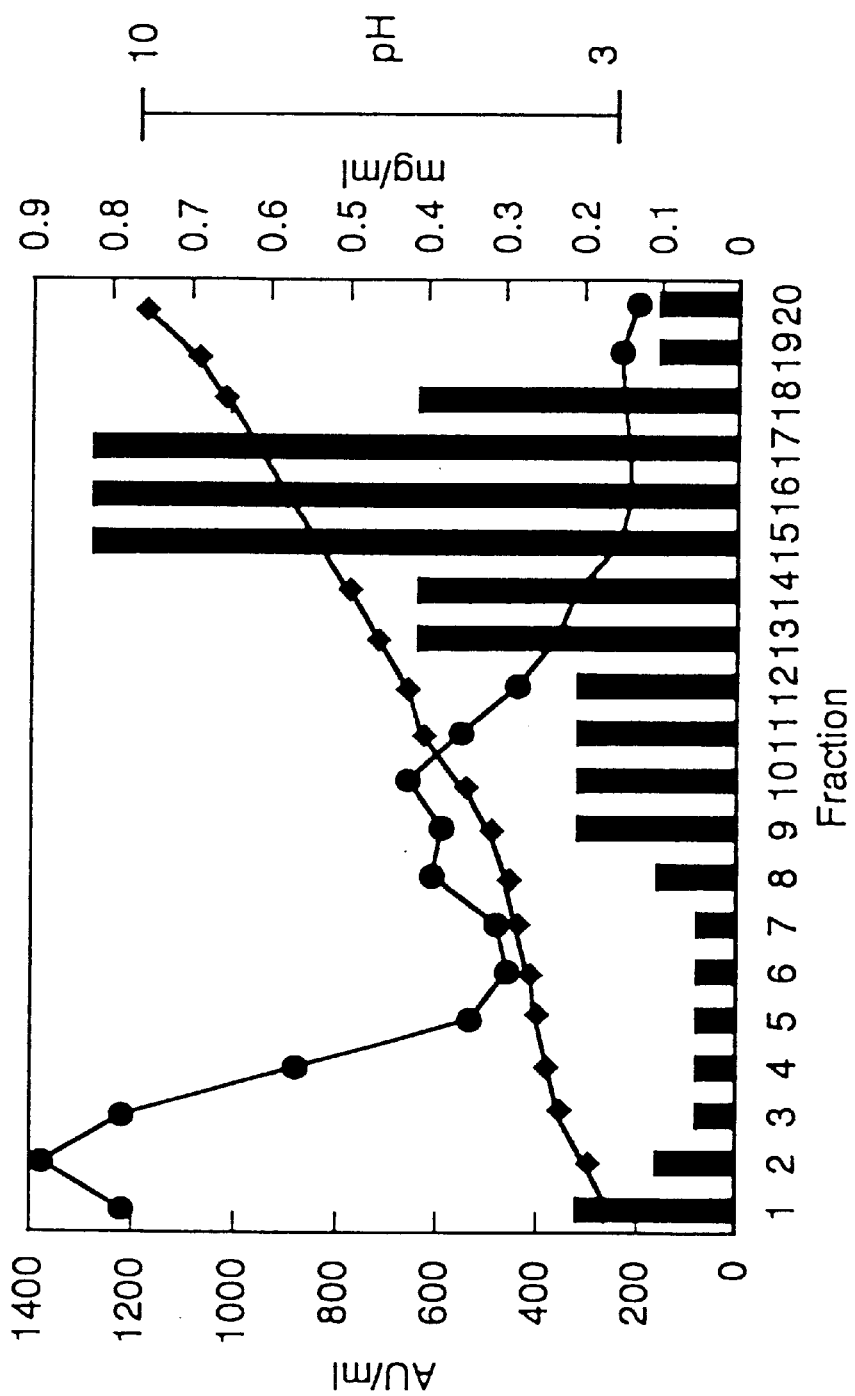
FIG. 7 includes three graphs illustrating the total protein (-●-), pH (-♦-), and BacR1 activity (bars) in twenty fractions obtained by Rotofor fractionation of ammonium sulfate-concentrated supernatants of *S. aureus* UT0007 cultures using ampholytes with a pH range of 3 to 10; the BacR1 activity of each fraction was measured by bactericidal assay (plate method)

BacR1 did not focus tightly, since BacR1 activity was found throughout all 20 harvested fractions (FIG. 7). The majority of the activity (46%) was contained in fractions 15 through 17, which is consistent with an apparent average pI of 7.7 for BacR1. BacR1 activity was not destroyed when ampholytes were removed by adsorption with AG® 501-X8 (D) resin (Bio-Rad, Richmond, Calif.). The inability of BacR1 to focus tightly makes isoelectric focusing an inefficient purification step due to the significant losses in total activity asociated with the remaining fractions. Since BacR1 activity was present throughout the pH gradient, it was concluded that the protein is hydrophobic. However, attempts to decrease hydrophobic interactions by incorporating 6 M urea during isoelectric focusing were unsuccessful (data not shown).

EXAMPLE 7

Determination of Stability of BacR1:

The stability of BacR1 was assessed by determining the activity of BacR1 by bactericidal assay (plate method) after exposure to various temperatures, environmental conditions, and enzymes (Table 2). Solutions of finally purified BacR1 at a concentration of 640 AU/ml were used in these stability experiments. BacR1 samples were held at various temperatures for 15 min, were held at pHs ranging from 3 to 11 at room temperature for 1 h, were incubated in 6M urea at room temperature for 1 h, or were incubated with 1 mg/ml of enzyme at room temperature for 1 h.

BacR1 can be classified as heat-stable since full bactericidal activity was retained after heating at 95° C. for 15 min. Additionally, BacR1 was not inactivated by treatment with 6 M urea, deoxyribonuclease (DNase), ribonuclease (RNase), or lysostaphin. However, proteinase K and trypsin destroyed bactericidal activity, confirming the proteinaceous nature of BacR1.

TABLE 2

Physical properties of BacR1.

| Treatment[a] | % Residual Activity |
|---|---|
| −20° C. | 100 |
| 4° C. | 100 |
| 25° C. | 100 |
| 37° C. | 100 |
| 95° C. | 100 |
| pH 3 to 11 | 100 |
| 6 M urea | 100 |
| DNase | 100 |
| RNase | 100 |
| lysostaphin | 100 |
| proteinase K | 0 |
| trypsin | 0 |

[a]BacR1 samples were held at the indicated temperatures for 15 min, and at room temperature for 1 h for all other treatments. Enzyme concentrations were 1 mg/ml.

EXAMPLE 8

Amino Acid Composition of BacR1:

Amino acid analysis was carried out at the Kansas State University Biotechnology facilities on an Applied Biosystems Model 420A Amino Acid analysis system (Applied Biosystems, Foster City, Calif.). Amino acid analysis revealed a high molar concentration of hydrophobic amino acids such as Ala, Pro, and Leu (Table 3), confirming the hydrophobic nature of BacR1. The association of BacR1 with other cellular proteins throughout the various purification steps described above may be due to its high degree of hydrophobicity. Furthermore, this hydrophobicity may account for the low yields of BacR1 during purification.

TABLE 3

Amino acid composition of BacR1.

| Amino Acid | Mole % |
| --- | --- |
| Asx | 11.91 |
| Glx | 7.87 |
| Ser | 5.36 |
| Gly | 21.16 |
| His | 2.58 |
| Arg | 0.79 |
| Thr | 0.86 |
| Ala | 8.78 |
| Pro | 12.55 |
| Tyr | 2.95 |
| Val | 3.91 |
| Met | 3.72 |
| Ile | 2.08 |
| Leu | 5.46 |
| Phe | 2.39 |
| Lys | 6.66 |
| Cys | 0.88 |
| Trp | Not Determined |

EXAMPLE 9
Bactericidal activity of BacR1 against *C. renale*:

Bactericidal activity of BacR1 against *C. renale* was determined by tube dilution analysis. An overnight culture of *C. renale* was used to innoculate fresh BHT-80 to an initial $A_{550}$ of 0.05. The fresh culture was then incubated at 37° C. with shaking at 220 rpm for 3 h to reach early log phase. At this point, 4 µl of the culture were added to each of tubes containing serially diluted, finally purified BacR1 in 0.4 ml BHT-80. The tubes were incubated at 37° C. with shaking at 220 rpm for 5 h. Percent survival of *C. renale* was determined by dividing the $A_{550}$ of each BacR1-containing culture by the A550 of a BacR1-free control culture. The $MIC_{50}$ represents the concentration of bacteriocin that caused a 50% inhibition of growth.

Figure 8:
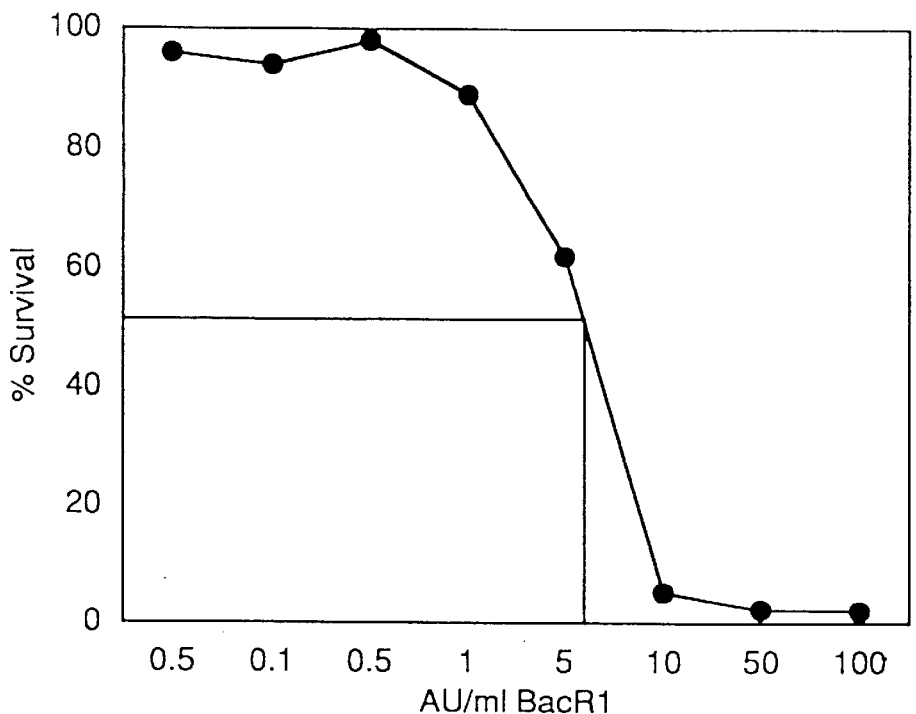
FIG. 8 includes a graph illustrating dose-dependent killing of *C. renale* by BacR1; cultures of *C. renale* ($10^8$ cells) were incubated with finally purified BacR1 at respective concentrations at 37° C. with shaking for 5 h, and the $A_{550}$ for each culture was measured; percent survival of *C. renale* (-●-) was determined by dividing the $A_{550}$ of each BacR1-containing culture by the $A_{550}$ of a BacR1-free control culture; a $MIC_{50}$ of approximately 6 AU/ml is indicated.
Figure 9:
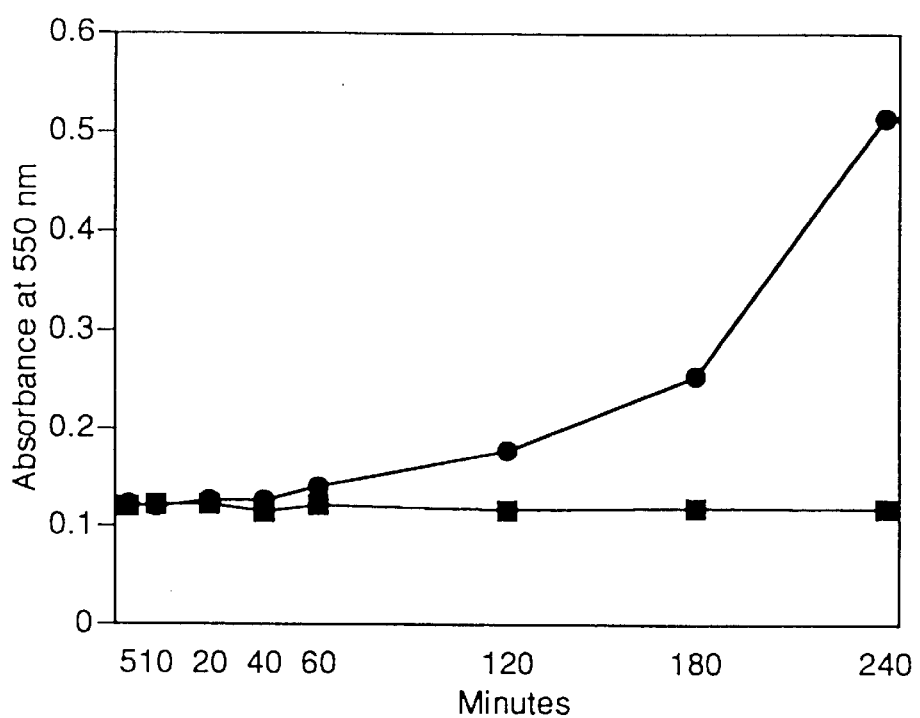
FIG. 9 includes a pair of graphs illustrating the effect of BacR1 on the viability *C. renale*; the $A_{550}$ of a culture of control cells (-●-) and a culture of cells incubated with BacR1 at a concentration of 100 AU/ml (-■-) was measured at respective times.
Figure 10:
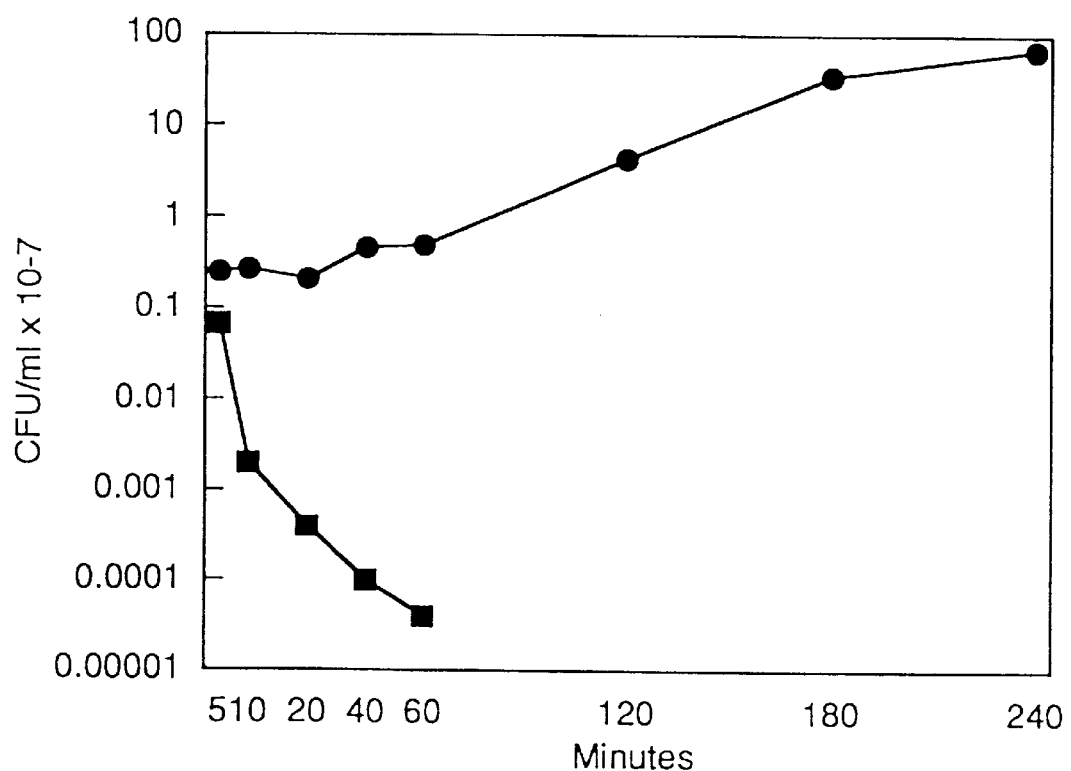
FIG. 10 includes a pair of graphs illustrating the effect of BacR1 on the viability *C. renale*; viable cell counts for a culture of control cells (-●-) and a culture of cells incubated with BacR1 at a concentration of 100 AU/ml (-■-) were determined at respective times.

BacR1 kills *C. renale* in a dose-dependent fashion, with a $MIC_{50}$ of approximately 6 AU/ml (FIG. 8). Furthermore, the killing is rapid in the absence of cell lysis as evidenced in FIGS. 9 and 10. No viable cells were detected after 120 min of exposure to BacR1. Purified BacR1 is bactericidal to *C. renale* because the cells do not recover after prolonged incubation with the bacteriocin. Such recovery would be observed with a bacteriostatic agent.

EXAMPLE 10
Determination of Inhibitory Spectrum of BacR1:

Bactericidal activity of BacR1 against various test organisms was determined using the bactericidal assay (plate method), except that *C. renale* was replaced by each test organism. BacR1 (purified through the first cycle of C4 reverse-phase chromatography) at a concentration of 1280 AU/ml was added to each plate. Both gram-positive and gram-negative organisms were sensitive to the lethal effects of BacR1 (Table 4). These data show that important pathogens such as *Bordetella brochoseptica, Pasteurella multocida, S. aureus*, and *Streptococcus suis* are all killed by BacR1. Moreover, *Moraxella bovis*, the agent causing infectious bovine keratoconjunctivitis (IBK), is especially sensitive to BacR1. IBK is a very serious disease of the eye in cattle (Hughes et al. 1970. J. Am. Vet. Med. Assoc. 157:443–451) and economic losses caused by it approach $150 million annually (U.S. Dept. Agriculture. 1976. ARS Natl. Res. Prog. No. 20420, p. 35–36). This infection causes severe pain and blindness which interferes with the ability of cattle to graze and subsequently gain weight normally. Treatment regimens for IBK based on prior art antibiotics have met with only limited success.

TABLE 4

Inhibitory spectrum of BacR1.

| Test Organism | Susceptibility[a] |
| --- | --- |
| *Actinobacillus pleuropneumoniae* | − |
| *Enterococcus faecalis* JH2-2 | − |
| *Escherichia coli* | − |
| *Haemophilus somnus* | − |
| *Klebseilla pneumoniae* | − |
| *Pseudomonas aeruginosa* | − |
| *Salmonella typhimurium* | − |
| *Streptococcus canis* | − |
| *Streptococcus equii* | − |
| *Bacillus subtilis* Marburg | + |
| *Bordetella brochoseptica* | + |
| *Bordetella pertussis* | + |
| *Corynebacterium diphtheriae* | + |
| *Corynebacterium pseudo-tuberculosis* Whetten 1 | + |
| *Corynebacterium renale* | + |
| *Haemophilus parasuis* | + |
| *Moraxella bovis* | + |
| *Pasteurella multocida* | + |
| *Staphylococcus aureus* 502A | + |
| *Staphylococcus aureus* 8325 | + |
| *Staphylococcus aureus* RN4220 | + |
| *Staphylococcus intermedias* | + |
| *Streptococcus porcinus* | + |
| *Streptococcus suis* | + |

[a]Susceptibility (+) of test organisms to BacR1 was demonstrated by bactericidal assays (plate method) in which zones of growth inhibition surrounded wells in indicator plates, while resistance (−) was demonstrated by the lack of zones of growth inhibition.

Additional analyses of the inhibitory spectrum of BacR1 reveals that additional organisms are sensitive, namely *Hemophilus parasuis, Bordatella pertussis, B. bronchoseptica* and *Moraxella bovis*. In addition, ten methicillin-resistant *S. aureus* (MRSA) strains were tested and all were very sensitive to BacR1. About 40% vancomycin-resistant strains of *Enterococcus faecalis* and *E. faecium* tested were sensitive to BacR1, while the remainder exhibit varying degrees of resistance. In terms of relative susceptibility, *C. renale* and *M. bovis* were equally (and most) sensitive. *S. aureus* was susceptible, but required higher doses of BacR1. The methicillin-resistant strains demonstrated increased sensitivity to BacR1. All sensitive genera were killed by reasonable amounts of BacR1. Strains of *S. aureus* that produce bacteriocin activity have the necessary immunity factors to protect themselves from the lethal effects of BacR1. Several important gram-negative pathogens were also found to be sensitive to BacR1. The broad spectrum of activity of BacR1 is a distinguishing feature that enhances its value as an antibacterial.

EXAMPLE 11
Identification of the BacR1 Gene and Operon

The BacR1 structural gene (SEQ ID No. 2) was identified by N-terminal sequencing of the purified BacR1 peptide, prepared as described previously. The peptide was subjected to mass spectrographic analysis, and exhibited only a single peak. The peptide was then subjected to sequencing by automated Edman degradation. Using a codon usage table made from Staphylococcal genomic sequence information, the peptide information was back-translated to construct an oligonucleotide probe. The probe was then used to identify a fragment of the pRW001 plasmid believed to contain the BacR1 structural gene. The sequence of this fragment was determined from sequence information previously accumulated for pRW001. The BacR1 operon was then identified by comparison of the BacR1 protein sequence to the deduced peptides arising from the DNA sequence. The sequence of the BacR1 operon is set forth as SEQ ID No. 4. The remaining genes in the BacR1 operon have been identified and provided with tentative designations by comparison to entries in the GenBank database. In the operon and following the BacR1 structural gene, is a homolog of the cylM gene of the cytolysin operon of *Enterococcus faecalis*, whose function is involved in the maturation (i.e., post-translational condensation and cyclization) of the pre-cytolysin. Next are an ATP-binding cassette transport protein (i.e., ABC-transporter gene), two additional biosynthesis genes (biol and bio2) that are related to lactococcin biosynthesis and modification, and finally a gene that appears to relate to the immunity function (nisF/epiF homologs of the nissin and epidermin immunity genes).

EXAMPLE 12

Cloning and Expression of BacR1

The entire BacR1 operon (SEQ ID No. 4) is cloned into the plasmid pUB110(Kan$^R$) and transformed into *Bacillus subtilis* competent cells. Transformants are placed on Trypticise Soy Agar plates containing Kanamycin and inoculated with *C. renale* (pUB 110) that is resistant to Kanamycin. Kanamycin-resistant clones of *B. subtilis* that also produce a zone of inhibition in the *C. renale* lawn are isolated. Alternately, transformants are plated on agar-containing bacteriocin and selected directly for resistance. The clones actively produce BacR1 and are tested to determine the amounts expressed. Purification of the expressed BacR1 is then carried out as described above. This system has the advantage of exploiting the ability of *B. subtilis* to produce extracellular proteins, and clones expressing BacR1 secrete it into the medium.

We claim:

1. An essentially pure peptide of SEQ ID No. 3.

2. A method of inhibiting the growth of cells in an environment capable of sustaining said growth comprising administering to the environment a cellular growth-inhibiting amount of recombinantly-derived BacR1 peptide.

3. An essentially pure therapeutic proteinaceous substance having a molecular weight under 4 kilodaltons, said substance being recombinantly derived and having at least about 80% sequence identity relative to SEQ ID No. 3.

4. The substance of claim 3, wherein said substance is dispersed in a liquid, said liquid with said substance dispersed therein having a specific activity of at least about 1000 antimicrobial units (AU) per milligram of protein.

5. The substance of claim 4, wherein said substance is dispersed in a liquid, said liquid with said substance dispersed therein having a specific activity of at least about 30,000 antimicrobial units per milligram of protein.

6. The substance of claim 3, wherein said substance is essentially protein.

7. The substance of claim 3, wherein amino acid residues selected from the group consisting of alanine, threonine, glycine and cysteine make up at least about 40% of the amino acid residues of the substance.

8. The substance of claim 3, wherein said substance at a concentration of 640 AU/ml in an aqueous solution retains its antimicrobial activity after being heated at 95° C. for up to 15 minutes.

9. The substance of claim 3, wherein said substance at a concentration of 640 AU/ml in an aqueous solution retains its antimicrobial activity after being treated at room temperature for 1 hour at pHs ranging from 3 to 11.

10. The substance of claim 3, wherein said substance at a concentration of 640 AU/ml in an aqueous solution retains its antimicrobial activity after being treated at room temperature for 1 hour with urea at a concentration of 6 M.

11. The substance of claim 3, wherein said substance at a concentration of 640 AU/ml in an aqueous solution retains its antimicrobial activity after being treated at room temperature for 1 hour with an enzyme at a concentration of 1 mg/ml, said enzyme being selected from the group consisting of deoxyribonuclease, ribonuclease, and lysostaphin.

12. The substance of claim 3, wherein said substance at a concentration of 1280 AU/ml has antimicrobial activity against a microorganism selected from the group consising of *Bacillus subtilis* Marburg, *Bordetella brochoseptica Bordetella pertussis, Corynebacterium diphtheriae, Corynebacterium renale, Haemophilus parasuis, Moraxella bovis, Pasteurella multocida, Staphylococcus aureus* 502A, *Staphylococcus aureus* 8325, *Staphylococcus intermedias, Streptococcus porcinus*, and *Streptococcus suis*.

13. A method of inhibiting the growth of cells in an environment capable of sustaining such growth comprising administering to said environment a cellular growth-inhibiting amount of the substance of claim 3.

14. An essentially purified therapeutic proteinaceous substance produced by *Staphylococcus aureus* having a molecular weight under 4 kilodaltons, wherein said substance at a concentration of 640 microbial units/ml in an aqueous solution retains essentially all of its antimicrobial activity after one or more of the following treatments: (1) heat treatment at 95° C. for 15 minutes, (2) treatment with 6 M urea at room temperature for 1 hour, and (3) treatment with deoxyribonuclease, ribonuclease, or lysostaphin at a concentration of 1 mg/ml at room temperature for 1 hour.

15. The method of claim 2, said recombinantly-derived BacR1 peptide being the sole peptide administered.

* * * * *

UNITED STATES PATENT AND TRADEMARK OFFICE
CERTIFICATE OF CORRECTION

PATENT NO.    : 6,043,219
DATED         : March 28, 2000
INVENTOR(S)   : John J. Iandolo and Scott S. Crupper It is certified that error appears in the above-identified patent and that said Letters Patent is hereby corrected as shown below:

<u>Column 1,</u>
Line 4, please insert the following paragraph: -- FEDERALLY SPONSORED RESEARCH/DEVELOPMENT PROGRAM This invention was made with government support under Grant AI17474 awarded by the National Institute Of Health. The government has certain rights in the invention. --

Signed and Sealed this

Eleventh Day of March, 2003

JAMES E. ROGAN
*Director of the United States Patent and Trademark Office*